United States Patent [19]

Snipes

[11] Patent Number: 4,629,621
[45] Date of Patent: Dec. 16, 1986

[54] ERODIBLE MATRIX FOR SUSTAINED RELEASE BIOACTIVE COMPOSITION

[75] Inventor: Wallace C. Snipes, Pine Grove Mills, Pa.

[73] Assignee: Zetachron, Inc., State College, Pa.

[21] Appl. No.: 633,604

[22] Filed: Jul. 23, 1984

[51] Int. Cl.$^4$ ............................................. A61J 3/10
[52] U.S. Cl. ........................................ 424/19; 424/22; 428/402.24
[58] Field of Search ................. 424/19, 22; 428/402.24

[56]   References Cited
       U.S. PATENT DOCUMENTS 3,336,155  8/1967  Rowe ................................... 424/19
    3,634,584  2/1969  Poole .................................. 424/19
    3,641,236  2/1972  Coppen et al. ......................... 424/19

Primary Examiner—John Kight
Assistant Examiner—M. L. Moore
Attorney, Agent, or Firm—Vorys, Sater, Seymour and Pease

[57]   ABSTRACT

A sustained release composition for releasing a biologically active compound into an aqueous liquid environment comprises said biologically active compound dispersed in a bioerodible matrix, the matrix comprising a mixture of 5 to 95% by weight of a polyethylene glycol having a molecular weight of from about 1000 to about 20,000, and 95 to 5% by weight of an erosion rate modifier which is an amphiphilic compound insoluble in the aqueous liquid.

Dosage forms comprising the erodible matrix are prepared by molding, particularly by injection molding.

83 Claims, No Drawings

ERODIBLE MATRIX FOR SUSTAINED RELEASE BIOACTIVE COMPOSITION

BACKGROUND OF THE INVENTION

1. Field of the Invention

This invention relates to sustained release compositions for bioactive compounds and more particularly to sustained release oral dosage forms incorporating a drug in an erodible matrix.

2. Description of the Prior Art

In chemotherapy of diseases it is frequently desirable to maintain the concentration of the therapeutic drug at a relatively constant level in the blood or organ being treated. One method for achieving this goal is to administer the drug continuously at a rate which balances its rate of metabolism and/or excretion. In a hospital environment this goal can be attained by intravenously administering a drug, but outside of such an environment this method of administration is impractical in the great majority of cases. Consequently, the most common method of administering a drug is orally, in the form of tablets, capsules, and the like, which preferably have sustained release characteristics. The drug released therefrom is usually absorbed from the gastrointestinal tract and reaches the target organ via the blood stream.

Among the various types of sustained release dosage forms which have been developed are erodible matrices, i.e., dosage forms wherein the drug is entrapped in a matrix which upon ingestion gradually decomposes in the intestinal fluid thereby releasing the drug for absorption. An example of such a dosage form is found in Schmitt, U.S. Pat. No. 4,346,709, wherein the device comprises a drug dispersed in a bioerodible polymer which is a poly(orthoester) or a poly(orthocarbonate) containing an erosion rate modifier. The erosion rate modifiers of Schmitt are mono- and polybasic organic acids which adjust the pH at the surface of the erodible matrix to accelerate or retard the decomposition of the polymer in the gastric or intestinal environment.

In a further example, Sothmann, et al., in U.S. Pat. No. 4,351,825, disclose a sustained release oral dosage form wherein a drug is dispersed in a matrix of a water-insoluble polymethacrylate, e.g., a copolymer of acrylic and methacrylic acid esters containing quaternary ammonium groups or a copolymer of methyacrylic acid and methyl methacrylate, which has an anionic character. The granules of the matrix material are mixed with the active drug and an erosion rate modifier which is an ester of a long chain fatty acid with glycerine for a long chain alcohol.

Additionally, Kleber, et al., in U.S. Pat. No. 4,333,919, disclose controlled release formulations comprised of a drug mixed with a copolymer of lactic and glycolic acids. The formulations may also contain adjuvants such as glyceryl distearate. The formulations are primarily intended for growth stimulants for ruminants. Accordingly, they are administered by filling open-ended steel cylinders with the formulations and placing the cylinders in the rumen of the animal. The filled steel cylinders remain in the rumen, and the growth stimulant is gradually released as the matrix is eroded by the rumen fluids.

It seems evident from these disclosures, and others, that the erodible formulations of the prior art have generally required specially prepared polymers, and that the rate of erosion of such polymers cannot always be adjusted to provide for preferential release of the drug in a particular portion of the gastrointestinal tract, e.g., in the stomach or small intestine.

Therefore, a need has continued to exist for an erodible matrix, prepared from readily available materials which are suitable for sustained release pharmaceutical formulations, wherein the rate of erosion can be substantially controlled.

SUMMARY OF THE INVENTION

Accordingly, it is an object of this invention to provide an oral, sustained release dosage form.

A further object is to provide an oral, sustained release dosge form incorporating an erosion rate modifier substance.

A further object is to provide an oral, sustained release dosage form whose formulaton and/or structure can be adjusted to release its medication either in the stomach or the small intestine.

A further object is to provide a sustained release composition containing a bioactive compound which is released by erosion of the matrix in an aqueous liquid environment.

A further object is to provide a liquid-erodible composition wherein the rate of erosion can be adjusted by incorporation of an erosion rate modifier.

A further object is to provide a liquid-erodible composition wherein the rate of erosion can be adjusted to vary with the pH of the surrounding aqueous liquid.

Additional objects will become apparent from the description of the invention which follows.

The objects of the invention are achieved by a composition capable of being eroded in an aqueous liquid environment comprising a. about 5% to about 95% by weight of a solid polyethylene glycol having a molecular weight from about 1000 to about 20,000, and b. about 95% to about 5% of an erosion rate modifier which is an amphiphilic compound insoluble in the aqueous liquid.

A sustained release dosage form according to the invention comprises a matrix of the erodible composition of the invention having dissolved or dispersed therein a bioactive compound to be released over a period of time.

DETAILED DESCRIPTION OF THE INVENTION AND PREFERRED EMBODIMENTS

The property of the composition of this invention which makes it useful in sustained release preparations of bioactive material is its erodible character. Because it is the surface of an erodible composition which dissolves or decomposes into the surrounding medium and the eroding liquid does not substantially penetrate its structure, it is possible to achieve superior control of the dissolution rate of the solid composition, so that it may be used in a variety of applications.

The erodible matrix of this invention is especially suitable for incorporating a drug to be administered over a period of time via the intestinal absorption route. It is formed from a composition comprising solid polyethylene glycol and an amphiphilic erosion rate modifier, and the kinetics of its drug release are determined by the properties of the matrix and the shape of the dosage form. Accordingly, the rate of release can be controlled by varying the size and shape of the dosage form as well as the proportion and type of the erosion rate modifier.

The solid polythylene glycol component of the erodible matrix of this invention may be any polyethylene glycol (PEG) having a molecular weight from about 1000 to about 20000. All of the polyethylene glycols in this range are solid materials which are soluble in water and which will slowly dissolve when in contact with an aqueous medium. Mixtures of polyethylene glycols of different molecular weights may also be used. A preferred PEG is that having a molecular weight of about 8000. The PEG component of the erodible matrix may be present in amounts ranging from about 5% to about 95% by weight of the erodible matrix, preferably from 40% to 80% by weight.

The erosion rate modifier is an insoluble amphiphile, that is, a material whose molecule possesses a hydrophilic portion and a lipophilic portion, usually located at opposite ends of a relatively elongated molecule. The presence of lipophilic portions in the erosion rate modifier slows down the rate at which the matrix is eroded when in contact with an aqueous liquid environment. Therefore, the rate of erosion can be slightly retarded by incorporating relatively small amounts of erosion rate modifier and greatly retarded by incorporating relatively large amounts of erosion rate modifier.

The erosion rate modifier can also be chosen to vary the rate of erosion under varying conditions of pH. For example, if the erosion rate modifier is a long chain fatty acid such as myristic acid, the erosion rate of the matrix will be relatively slow in acid media wherein the carboxyl group of the myristic acid is not ionized and the amphiphilic molecule is accordingly relatively hydrophobic. On the other hand, under basic conditions the carboxyl group is ionized, and therefore hydrophilic, which makes the erosion rate considerably faster. Evidently, a dosage form made from such a formulation releases relatively little of a drug in the acidic environment of the stomach, but subsequently more freely releases the drug in the basic environment of the small intestine. In the event that erosion of the matrix in the stomach is desired, then erosion rate modifiers having basic groups which are ionized under acidic conditions can be incorporated in the matrix composition.

The erosion rate modifier can also be chosen to compensate for the effects of charged forms of the bioactive compound on the erosion rate. When the bioactive compound, e.g., a drug, is present in the matrix of the invention in amounts greater than about 2-3% by weight of the total composition, the ionic character of the drug can affect the rate of erosion at various pH's of the eroding environment. For, example if the erodible matrix contains a basic drug, which will assume a positive charge in the acidic environment of the stomach, thereby increasing the erosion rate, an acidic erosion rate modifier, e.g., a long chain fatty acid such as myristic acid, may be used as an erosion rate modifier. The acid will remain un-ionized in the acidic environment of the stomach and thereby act to retard the erosion rate and counterbalance the effect of the basic drug.

Use of erosion rate modifiers devoid of ionizable hydrophilic groups, such as long chain aliphatic alcohols, results in an erodible matrix whose rate of erosion is not greatly affected by the pH of the environment.

The erosion rate modifier may be present in the erodible compositions of this invention in amounts of about 95% to about 5% by weight, preferably from about 60% to about 20% by weight.

Suitable erosion rate modifiers include $C_{12}$–$C_{20}$ fatty acids, such as lauric acid, myristic acid, palmitic acid, stearic acid, and arachidic acid; $C_{12}$–$C_{20}$ alcohols, such as lauryl alcohol, myristyl alcohol, palmityl alcohol, stearyl alcohol and arachidyl alcohol, amphiphilic esters of fatty acids with glycerol, particularly monoesters of $C_{12}$–$C_{20}$ fatty acids such as glyceryl monopalmitate, $C_{12}$–$C_{20}$ amines such as lauryl amine, myristyl amine, palmityl amine, stearyl amine and arachidyl amine, and amides of $C_{12}$–$C_{20}$ fatty acids.

In various dosage forms embodiments of this invention, the rate of drug release can be controlled by varying the shape of the dosage form or by coating the surface of the dosage form. For example, an erodible dosage form of the invention may have a cylindrical shape wherein the height of the cylinder is much greater than the diameter, so that most of the area of the cylinder exposed to the erosive action of the aqueous liquid medium is constituted by the curved peripheral surface of the cylinder. When such a cylinder is immersed in a liquid medium the peripheral surface of the cylinder will be eroded. As the diameter of the cylinder decreases though its erosion, the area of the peripheral surface exposed to the erosive action of the aqueous liquid environment decreases proportionally. Therefore, the dosage form will erode at a rate which will provide approximately first order drug release kinetics. If a cylindrical dosage form has a relatively small height compared with its diameter, so that most of the exposed area is provided by the bases of the cylinder, the eroding surface area of the dosage form will not change greatly as erosion proceeds. In this case the rate of drug release will be substantially constant, i.e., the drug release kinetics will be approximately zero order.

In another embodiment, the surface of the dosage form can be partially coated with a liquid-impervious coating so that only certain surfaces of the dosage form are exposed to the erosive action of the medium. This method also allows for adjusting the kinetics of drug release. For example, if a cylindrical dosage form is coated on its curved peripheral surface so that only the ends of the cylinder are exposed to the erosive action of the medium, the area of the dosage form exposed to erosive action will not change with time. In this embodiment, therefore, the drug will be released at a constant rate, i.e., the release kinetics will be approximately zero order.

In order to assure that the rate of drug release will actually remain substantially constant for this coated cylindrical dosage form, it is necessary that the coating be non-self-supporting. If the coating is self-supporting it will extend beyond the ends of the cylindrical portion remaining after a portion of the dosage form has been eroded. This extension will interfere with the access of the eroding aqueous liquid medium to the ends of the cylinder and will, accordingly, affect the kinetics. Therefore, the preferred coating for this type of dosage form is a very thin friable material which is not self-supporting. With such a coating, any portion extending beyond the end of the cylinder after the immediately underlying matrix has been eroded will be broken off as the dosage form is subjected to agitation in the gastrointestinal tract, thus keeping the uncoated ends of the cylinder fully exposed to the erosive action of the medium.

In most cases it will be convenient to apply the coating material in the form of a melt which solidifies by cooling on the surface of the dosage form. Preferred coating materials are long chain fatty acids having 12 to 20 carbon atoms. Such acids include lauric acid, myristic acid, palmitic acid, stearic acid and arachidic acid. The thickness of the coating will typically be from about 0.02 mm to about 0.5 mm.

Additional ingredients can be incorporated into the erodible composition of this invention to modify and/or control the properties of the composition. For example, in order to improve the compatibility between the polyethylene glycol and the erosion rate modifier and prevent phase separation when the molten composition is cooled, a modified polyethylene glycol wherein the OH groups at one or both ends are esterified with long chain fatty acids may be added to the mixture. Suitable long chain fatty acids are aliphatic fatty acids having from about 12 to about 20 carbon atoms such as those disclosed above. Preferred polyethylene glycols to be used in preparing the esterified PEG compatibility enhancers are those haivng a molecular weight from about 200 to 10000, preferably from about 200 to about 2000. PEG 400 and PEG 600 are particularly preferred materials for preparing the esterified PEG's. For example, the esterified PEG's may be the monoesters and prefereably the lauric or stearic ester. More preferred esters are the diesters, particularly the dilauroyl and distearoyl esters. These modified polyethylene glycols are prepared by conventional esterification procedures well known to those skilled in the art, such as reacting the polyethylene glycol with the acid chloride of the chosen acid. The modified polyethylene glycol may be incorporated into the compositions of this invention in any effective amounts, such as in an amount up to about 10% by weight, preferably from about 0.1% to about 10% by weight, and particularly about 2% by weight.

Starch may also be added to the erodible mixture of this invention as a disintegrant in order to adjust the erosion rate. The starch tends to enhance the erodible characteristics of the composition by causing the solid material to dissolve from the surface without penetration of the aqueous liquid into the interior of the solid form. Any type of starch may be used, particularly a pharmaceutically acceptable and readily available form of starch, such as cornstarch. Starch may be present in amounts of from about 5% by weight to about 60% by weight, preferably from about 10% by weight to about 50% by weight, and more preferably from about 20% by weight to about 40% by weight.

Molding adjuvants may also be added to the compositions of this invention. It has been found that the addition of a polyethylene oxide (PEO) having a molecular weight (MW) from about 100,000 to about $5 \times 10^6$ has beneficial effects on the viscosity and plasticity of the composition. This provides for easier mold filling and release of molded forms from the molds, especially when molded dosage forms of this invention are prepared by injection molding. The PEO may be present in an effective amount up to about 2% by weight, preferably from about 0.05% by weight to about 1% by weight, and most preferably about 0.1% by weight. It will be appreciated by those skilled in the art that injection molding of compositions containing a relatively large number of ingredients, such as the compositions of this invention, is not common. Hence, some experimentation may be required to determine the exact amount of molding adjuvant needed for a given composition.

The erodible matrix of this invention is useful wherever controlled release of a material into an aqueous liquid environment is desired. Such an erodible material may be used, for example, without an incorporated drug as a coating for a substance designed for a delayed dissolution after immersion in an aqueous liquid. It may serve a similar function when employed as a plug for a container intended to release a material on a delayed-action basis when immersed or contacted with an aqueous liquid.

The erodible composition of this invention may also contain an ecological agent dispersed therein in order to provide for gradual release of the ecological agent into into an aqueous liquid environment. An ecological agent is defined for purposes of this invention as a non-pharmaceutical substance which has a biological effect on plants or animals in the environment. An ecological agent may be a pesticide, such as an insecticide or herbicide, a fertilizer, a pheromone, a plant growth hormone, or the like. When dosage forms made from compositions containing such bioactive ingredients contact an aqueous liquid environment the bioactive materials are gradually released into the environment. Accordingly, the compositions of this invention are useful for releasing such ecological agents into bodies of water or into a land environment where they may release their active agents by contact with rain or standing water, so as to maintain an effective concentration of the agent in the environment for a relatively long period of time.

It is preferred to use the erodible matrix of this invention as a carrier for sustained release pharmaceuticals administered orally to individuals in need of a relatively constant concentration of medication. The drugs may be locally or systemically acting drugs, and may be selected from among any group wherein a steady concentration of the drug in the organism is desired. Accordingly, the drug may be selected from among analgesic, anorexic, antiarthritic, antibacterial, antibiotic, anticonvulsant, anti-depressant, antidiabetic, anti-fungal, antihistaminic, anti-hypertensive, anti-inflammatory, anti-neoplastic, antiparkinsonism, antipyretic, anticholinergic, anti-inflammatory, anesthetic, antimicrobial, antiviral, anti-ulcer, bronchodilator, cardiovascular, contraceptive, central nervous system affecting, inotrophic, vasodilator, vasoconstrictor, decongestant, diuretic, hypoglycemic, hormone, hypnotic, hematinic, electrolyte supplement, germicidal, muscle relaxant, parasympathetolytic, parasympathetomimetic, tranquilizer, ophthalmic, psychostimulant, vitamin, and the like drugs. The drugs can be administered in the form of the parent compound as well as in the form of pharmaceutically acceptable salts, and precursors.

Preferred drugs for use in the dosage forms prepared according to the invention include clonidine, theophylline, dipyridamole, hydrochlorothiazide, scopolamine, indomethacin, furosemide, potassium chloride and the like.

The drug to be released from the dosage form of the invention may be incorporated into the erodible matrix simply by dissolving it in the molten matrix or mixing it therewith.

The proportions of drug and erodible matrix in the dosage forms of this invention may vary within wide limits. Because some drugs are effective in very small doses and others require relatively large doses for effect, the proportions will vary depending on the amount of drug which must be incorporated into the unit dosage form. Accordingly, the drug may be constitute in an effective amount up to about 70% by weight of the composition. More preferably the drug will constitute from about 0.1% to about 50% by weight of the composition, with the balance being the erodible matrix.

The unit dosage forms of the invention can be prepared by conventional procedures such as compression molding, tableting, extrusion, and injection molding. It is preferred that the dosage forms of the invention be non-porous in order that the erosion will proceed from the surface of the dosage form. Such non-porous dosage forms are best prepared by solidification of a molten form of the composition containing all ingredients of the composition, and injection molding is especially useful for that purpose. Indeed, the dosage forms of the invention are especially adapted to production by injection molding because the erodible matrix composition of the invention has a relatively low melting temperature, and hence the injection molding can be carried out at a temperature which is not detrimental to the drug contained in the dosage form.

The preferred dosage forms of the invention have a cylindrical shape with a diameter of about 3 mm to about 8 mm, and preferably about 5 mm. The length of the cylindrical dosage form is typically about 5 mm to about 20 mm, and is preferably about 10 mm. The preferred dosage forms may be coated on their peripheral cylindrical surfaces with a liquid-impervious non-self-supporting coating as discussed above.

The sustained release compositions of this invention are prepared by the following general procedure.

A premeasured amount of a polyethylene glycol is melted in a vessel, e.g., a kettle provided with a steam jacket or a heating mantle and equipped with a stirring mechanism. A temperature of about 85° C. is sufficient to melt any of the polyethylene glycols. The premeasured amount of the insoluble amphiphile is then added either as a molten liquid or as a solid. It is preferred to melt the insoluble amphiphile and add it slowly to the stirred molten PEG. The long chain fatty amphiphiles useful in the compositions of this invention are generally molten at the temperature of the molten PEG and can be readily mixed with the PEG. The bioactive agent, drug or the like is then added and dissolved in the molten mixture. Other ingredients, such as disintegrants (e.g., starch), molding adjuvants (e.g., polyethylene oxide), and the like are then added and the mixture is thoroughly blended. Dosage forms may then be formed directly from the molten mixture by the procedures outlined above.

The invention will now be further elucidated by the following examples which are included by way of illustration only and are not intended to be limiting. In the examples all percentages and parts are weight unless otherwise specified.

EXAMPLE 1

This example illustrates the preparation of dosage forms of the invention containing polyethylene glycols of various molecular weights.

A series of compositions were prepared having the following compositions:

|   |   |   |
|---|---|---|
| A. | PEG-1000 | 37.5% |
|   | Myristic acid | 15% |
|   | Starch | 22.5% |
|   | Indomethacin | 25% |
| B. | PEG-4000 | 37.5% |
|   | Myristic acid | 15% |
|   | Starch | 22.5% |
|   | Indomethacin | 25% |

-continued

|   |   |   |
|---|---|---|
| C. | PEG-8000 | 37.5% |
|   | Myristic acid | 15% |
|   | Starch | 22.5% |
|   | Indomethacin | 25% |
| D. | PEG-20,000 | 37.5% |
|   | Myristic acid | 15% |
|   | Starch | 22.5% |
|   | Indomethacin | 25% |

Cylindrical dosage forms were molded from the compositions A–D by pouring the molten compositions into open-ended plastic molds made of polyethylene having a diameter of about 6 mm and allowing the melt to cool to room temperature. The solidified composition was then extruded from the molds and cut into lengths to prepare cylindrical dosage forms. In this way dosage forms having a diameter of about 6 mm and a length of about 14 mm and weighing about 0.44 g each were prepared.

The sutained release properties of the dosage forms were then tested by the following procedure:

Simulated intestinal fluid (SIF) was prepared by the following procedure:

(1) 6.8 g of monobasic potassium phosphate were dissolved in 250 ml of water.

(2) 190 ml of 0.2 N NaOH was added with stirring.

(3) 400 ml of water and 10 ml of pancreatin were added.

(4) The pH of the solution was adjusted with 0.2 N NaOH to 7.5±0.1.

(5) The solution was diluted with water to 1000 ml.

Each of the cylindrical dosage forms was placed in 80 ml of SIF at 37° C. and subjected to gentle agitation. The amount of drug released was monitored by measuring the optical density of the aqueous medium at an absorption peak of indomethacin at intervals using an ultraviolet spectrophotometer. Each of the dosage forms was found to release the drug gradually over a period of several hours.

Cylindrical dosage forms of the same size and shape as above were prepared from each of the compositions A–D, but these cylinders were coated on their cylindrical surfaces with myristic acid by dipping the cylinders in molten myristic acid, withdrawing the cylinders and allowing the myristic acid coating to cool and harden, and then scraping the coating from the ends of the cylinders. These dosage forms were tested in SIF by the same procedure as the uncoated dosage forms. They also were found to release the drug over a period of several hours with the drug release occurring at an approximately constant rate.

EXAMPLE 2

This example illustrates variation of the fatty acid erosion rate modifier.

Several dosage forms were prepared by the procedure of Example 1 having the following compositions:

|   |   |   |
|---|---|---|
| A. | PEG-8000 | 37.5% |
|   | Myristic acid | 15% |
|   | Starch | 22.5% |
|   | Indomethacin | 25% |
| B. | PEG-8000 | 37.5% |
|   | Palmitic acid | 15% |
|   | Starch | 22.5% |
|   | Indomethacin | 25% |
| C. | PEG-8000 | 37.5% |
|   | Stearic acid | 15% |

| | |
|---|---|
| Starch | 22.5% |
| Indomethacin | 25% |

The dosage forms were tested by the procedure of Example 1 and were found to release the drug over a period of several hours at a relatively constant rate.

EXAMPLE 3

This example illustrates another composition of the invention incorporating additional ingredients.

A sustained release composition was prepared by the general procedure disclosed above having the following composition:

| | |
|---|---|
| PEG-8000 | 27% |
| Palmitic acid | 13% |
| PEG 400 monostearate | 10% |
| PEO (MW 5 × 10$^6$) | 0.1% |
| Cornstarch | 49.8% |
| Clonidine HCl | 0.1% |

The molten mixture was poured onto a surface and allowed to cool and solidify. The solid material was then granulated and fed into an injection molding machine to form dosage forms according to the invention.

EXAMPLE 4

This example illustrates the preparation of dosage forms whose release rate varies with pH.

Uncoated dosage forms of the following composition were prepared by the procedure of Example 1 above:

| | |
|---|---|
| PEG-8000 | 2.8 g |
| Myristic acid | 1.1 g |
| Starch | 1.6 g |
| Sodium bicarbonate | 0.5 g |
| Indomethacin | 2.0 g |

Simulated gastric fluid was prepared by dissolving 2 g of sodium chloride and 3.2 g of pepsin in 7 ml of hydrochloric acid, then diluting the solution to a volume of 1000 ml. The pH of the SGF was about 1.2.

The dosage forms were tested by the procedure of Example 1 in SIF and SGF. It was found that the rate of drug release was substantially faster in SIF.

EXAMPLE 5

This example illustrates preparation of PEG esters.

PEG-8000 was melted in a vessel equipped with a stirrer and heated to 100° C. An amount of myristyl chloride equivalent to one half of the terminal hydroxyl groups of the PEG was melted and added dropwise to the molten PEG with continuous stirring. Chloroform was added to the mixture and the solution was filtered through filter paper (Whatman No. 4) and allowed to stand overnight to evaporate the solvent. The remaining solvent was evaporated the next day by heating at 60° C. The material so obtained was a hard waxy solid having a melting point of about 60° C.

EXAMPLE 6

This example illustrates the preparation of dosage forms of the invention using various drugs.

Sustained release compositions were prepared by the general procedure disclosed above having the following compositions:

| | | |
|---|---|---|
| A. | PEG (MW 3,350) | 37% |
| | Stearyl alcohol | 15% |
| | Theophylline | 50% |
| B. | PEG 8000 | 30% |
| | Myristic acid | 20% |
| | PEG 400 monostearate | 10% |
| | PEO (MW 5 × 10$^6$) | 0.1% |
| | Corn starch | 24.9% |
| | Dipyridamole | 15% |
| C. | PEG-8000 | 2.8 g |
| | Myristic acid | 1.2 g |
| | Starch | 1.8 g |
| D. | PEG-8000 | 1.5 g |
| | Myristic acid | 0.6 g |
| | Starch | 0.9 g |
| | Furosemide | 1.0 g |
| E. | PEG-8000 | 5% |
| | Myristic acid | 10% |
| | Starch | 15% |
| | Flubiprofen | 70% |
| F. | PEG-1000 | 0.7 g |
| | PEG-8000 | 0.7 g |
| | PEG-20000 | 0.7 g |
| | Myristic acid | 1.0 g |
| | Palmitic acid | 1.0 g |
| | Stearic acid | 1.0 g |
| | Starch | 0.9 g |
| | KCl | 6.0 g |
| G. | PEG-8000 | 50% |
| | Glyceryl monostearate | 5% |
| | Starch | 20% |
| | Dipyridamole | 25% |

EXAMPLE 7

This example illustrates a dosage form of this invention incorporating a pesticide.

A composition of the invention was prepared by the procedure of Example 1 having the following composition:

| | |
|---|---|
| PEG-8000 | 37.5% |
| Myristic acid | 15.0% |
| Starch | 22.5% |
| Carbofuran | 25.0% |

Cylindrical dosage forms (uncoated) were prepared by the procedure of Example 1. These dosage forms were found to erode over a period of about one day in an aqueous environment.

EXAMPLE 8

This example illustrates the preparation of a coated dosage form of the invention.

A composition was prepared by the procedure of Example 1 having the following composition:

| | |
|---|---|
| PEG-3350 | 27% |
| Myristic acid | 13% |
| PEG-400 distearate | 2% |
| Potato starch | 13% |
| Quinidine · 2H$_2$SO$_4$ | 45% |

After mixing the molten composition was poured onto a surface and allowed to cool and harden. The hardened composition was then granulated and introduced into an extrusion apparatus. A cylindrical stream was extruded from the apparatus and coextruded therewith, so as to form a continuous coating over the extruded cylinder, was a liquid impervious coating having the following composition:

| Cetyl alcohol | 99% |
| --- | --- |
| Diethyl phthalate | 1% |

The extruded cylinder was then cut into dosage forms having a length of about 10 mm and dosage forms were tested as in Example 1 and found to release the drug over a period of time.

The invention having now been fully described, it will be apparent to one skilled in the art that many variations can be made without departing from the spirit of the invention.

What is claimed is:

1. A composition erodible by an aqueous liquid comprising
   5 to 95% by weight of a polyethylene glycol having a molecular weight of from about 1000 to about 20,000, and
   95 to 5% by weight of an erosion rate modifier which is an amphiphilic compound insoluble in said aqueous liquid, the molecular structure of said amphiphilic compound having a lipophilic portion and a hydrophilic portion.

2. The composition of claim 1 wherein said polyethylene glycol has a molecular weight of about 8000.

3. The composition of claim 1 wherein said erosion rate modifier is a $C_{12}$–$C_{20}$ fatty acid.

4. The composition of claim 3 wherein said fatty acid is selected from the group consisting of myristic acid and stearic acid.

5. The composition of claim 1 additionally comprising a substance which increases the compatibility of the polyethylene glycol and the erosion rate modifier.

6. The composition of claim 5 wherein said substance is a polyethylene glycol having a molecular weight from about 200 to about 10000 and having at least one of its terminal OH groups esterified with a $C_{12}$–$C_{20}$ fatty acid.

7. The composition of claim 6 wherein said polyethylene glycol is polyethylene glycol 400.

8. The composition of claim 7 wherein said substance is polyethylene glycol 400 having at least one of its terminal OH groups esterified with stearic acid.

9. The composition of claim 1 additionally comprising a disintegrant.

10. The composition of claim 9 wherein said disintegrant is starch.

11. The composition of claim 1 additionally comprising a molding adjuvant.

12. The composition of claim 11 wherein said molding adjuvant is polyethylene oxide having a molecular weight of 100,000 to 5,000,000.

13. A sustained release composition for releasing a biologically active compound into its surrounding environment comprising said biologically active compound dispersed in a matrix which, when contacted with an aqueous liquid, erodes progressively, said matrix comprising a mixture of
   5 to 95% by weight of a polyethylene glycol having a molecular weight of from about 1000 to about 20,000, and
   95 to 5% by weight of an erosion rate modifier which is an amphiphilic compound insoluble in said aqueous liquid, the molecular structure of said amphiphilic compound having a lipophilic portion and a hydrophilic portion.

14. The composition of claim 13 wherein said polyethylene glycol has a molecular weight of about 8000.

15. The composition of claim 13 wherein said erosion rate modifier is a $C_{12}$–$C_{20}$ fatty acid.

16. The composition of claim 15 wherein said fatty acid is selected from the group consisting of myristic acid and stearic acid.

17. The composition of claim 13 additionally comprising a substance which increases the compatibility of the polyethylene glycol and the erosion rate modifier.

18. The composition of claim 17 wherein said substance is a polyethylene glycol having a molecular weight from about 200 to about 10000 and having at least one of its terminal OH groups esterified with a $C_{12}$–$C_{20}$ fatty acid.

19. The composition of claim 18 wherein said polyethylene glycol is polyethylene glycol 400.

20. The composition of claim 19 wherein said substance is polyethylene glycol 400 having at least one of its terminal OH groups esterified with stearic acid.

21. The composition of claim 13 additionally comprising a disintegrant.

22. The composition of claim 21 wherein said disintegrant is starch.

23. The composition of claim 13 additionally comprising a molding adjuvant.

24. The composition of claim 23 wherein said molding adjuvant is polyethylene oxide having a molecular weight of 100,000 to 5,000,000.

25. A sustained release composition for releasing a biologically active compound into its surrounding environment comprising a pharmaceutically active compound or non-toxic pharmaceutically acceptable salt of said pharmaceutically active compound dispersed in a matrix which, when contacted with an aqueous liquid, erodes progressively, said matrix comprising a mixture of
   5 to 95% by weight of a polyethylene glycol having a molecular weight of from about 1000 to about 20,000, and
   95 to 5% by weight of an erosion rate modifier which is an amphiphilic compound insoluble in said aqueous liquid, the molecular structure of said amphiphilic compound having a lipophilic portion and a hydrophilic portion.

26. The composition of claim 25 wherein said compound is clonidine.

27. The composition of claim 25 wherein said compound is dipyridamole.

28. The composition of claim 25 wherein said compound is hydrochlorothiazide.

29. The composition of claim 25 wherein said compound is furosemide.

30. The composition of claim 25 wherein said compound is indomethacin.

31. The composition of claim 25 wherein said compound is scopolamine.

32. The composition of claim 25 wherein said compound is a bronchodilator.

33. The composition of claim 32 wherein said bronchodilator is theophylline.

34. The composition of claim 25 wherein said compound is quinidine.

35. The composition of claim 25 wherein said compound is naproxen.

36. The composition of claim 25 wheein said compound is propranolol.

37. The composition of claim 25 wherein said compound is a salicylate.

38. The composition of claim 37 wherein said salicylate is aspirin.

39. The composition of claim 25 wherein said compound is nitroglycerin.

40. The composition of claim 25 wherein said compound is isosorbide dinitrate.

41. A sustained release composition for releasing an ecologically active compound into its surrounding environment comprising said ecologically active compound dispersed in a matrix which, when contacted with an aqueous liquid, erodes progressively, said matrix comprising a mixture of
- 5 to 95% by weight of a polyethylene glycol having a molecular weight of from about 1000 to about 20,000, and
- 95 to 5% by weight of an erosion rate modifier which is an amphiphilic compound insoluble in said aqueous liquid, the molecular structure of said amphiphilic compound having a lipophilic portion and a hydrophilic portion.

42. The composition of claim 41 wherein said ecologically active compound is a fertilizer.

43. The composition of claim 41 wehrein said ecologically active compound is a pesticide.

44. The composition of claim 41 wherein said ecologically active compound is an insecticide.

45. The composition of claim 41 wherein said ecologically active compound is an herbicide.

46. A sustained release dosage form for releasing a biologically active compound into an aqueous liquid environment comprising a non-porous solid erodible matrix having dispersed therein a biologically active compound, said matrix comprising a mixture of
- 5 to 95% by weight of a polyethylene glycol having a molecular weight of from about 1000 to about 20,000, and
- 95 to 5% by weight of an erosion rate modifier which is an amphiphilic compound insoluble in said aqueous liquid, the molecular structure of said amphiphilic compound having a lipophilic portion and a hydrophilic portion.

47. The dosage form of claim 46 wherein said polyethylene glycol has a molecular weight of about 8000.

48. The dosage form of claim 46 wherein said erosion rate modifier is a $C_{12}$–$C_{20}$ fatty acid.

49. The dosage form of claim 48 wherein said fatty acid is selected from the group consisting of myristic acid and stearic acid.

50. The dosage form of claim 46 additionally comprising a substance which increases the compatibility of the polyethylene glycol and the erosion rate modifier.

51. The dosage form of claim 50 wherein said substance is a polyethylene glycol having a molecular weight from about 200 to about 10000 and having at least one of its terminal OH groups esterified with a $C_{12}$–$C_{20}$ fatty acid.

52. The dosage form of claim 51 wherein said polyethylene glycol is polyethylene glycol 400.

53. The dosage form of claim 52 wherein said substance is polyethylene glycol 400 having at least one of its terminal OH groups esterified with stearic acid.

54. The dosage form of claim 46 additionally comprising a disintegrant.

55. The dosage form of claim 54 wherein said disintegrant is starch.

56. The dosage form of claim 46 additionally comprising a molding adjuvant.

57. The dosage form of claim 56 wherein said molding adjuvant is polyethylene oxide having a molecular weight of 100,000 to 5,000,000.

58. The dosage form of claim 46 wherein said biologically active compound is a pharmaceutically active compound or non-toxic pharmaceutically acceptable salt of said compound and said dosage form contains an effective amount of said compound or said salt.

59. The dosage form of claim 58 wherein said compound is clonidine.

60. The dosage form of claim 58 wherein said compound is dipyridamole.

61. The dosage form of claim 58 wherein said compound is hydrochlorothiazide.

62. The dosage form of claim 58 wherein said compound is furosemide.

63. The dosage form of claim 58 wherein said compound is indomethacin.

64. The dosage form of claim 58 wherein said compound is scopolamine.

65. The dosage form of claim 58 wherein said compound is a bronchodilator.

66. The dosage form of claim 65 wherein said bronchodilator is theophylline.

67. The dosage form of claim 58 wherein said compound is quinidine.

68. The dosage form of claim 58 wherein said compound is naproxen.

69. The dosage form of claim 58 wherein said compound is propranolol.

70. The dosage form of claim 58 wherein said compound is a salicylate.

71. The composition of claim 70 wherein said salicylate is aspirin.

72. The dosage form of claim 58 wherein said compound is nitroglycerin.

73. The dosage form of claim 58 wherein said compound is isosorbide dinitrate.

74. The dosage form of claim 46 wherein said dosage form has the shape of a cylinder.

75. The dosage form of claim 74 wherein said cylinder has a diameter from about 3 mm to about 8 mm.

76. The dosage form of claim 75 wherein said cylinder has a diameter of about 6 mm.

77. The dosage form of claim 74 wherein said cylinder has a length from about 5 mm to about 20 mm.

78. The dosage form of claim 77 wherein said cylinder has a length of about 10 mm.

79. The dosage form of claim 74 additionally comprising at least a partial coating of a liquid impermeable non-self-supporting coating.

80. The dosage form of claim 79 wherein said coating comprises a solid $C_{12}$–$C_{20}$ fatty acid.

81. The dosage form of claim 80 wherein said coating comprises myristic acid.

82. The dosage form of claim 80 wherein said coating comprises palmitic aicd.

83. The dosage form of claim 79 wherein said dosage form has a cylindrical shape and is coated on its peripheral cylindrical surface with a liquid-impervious non-self-supporting coating.

* * * * *